(12) United States Patent
Seki

(10) Patent No.: US 6,258,096 B1
(45) Date of Patent: Jul. 10, 2001

(54) EXTRAMEDULLARY FEMORAL CLAMP GUIDE SYSTEM FOR TOTAL KNEE ARTHROPLASTY

(75) Inventor: Takahiro Seki, Ryotsu (JP)

(73) Assignee: Mizuho Ika Kogyo Kabushiki Kaisha, Tokyo-To (JP)

(*) Notice: Subject to any disclaimer, the term of this patent is extended or adjusted under 35 U.S.C. 154(b) by 0 days.

(21) Appl. No.: 09/543,172

(22) Filed: Apr. 5, 2000

(30) Foreign Application Priority Data

Apr. 7, 1999 (JP) .................................. 11-100356

(51) Int. Cl.[7] .................................. A61B 17/15
(52) U.S. Cl. ........................... 606/88; 606/86; 606/102
(58) Field of Search .................... 606/86, 87, 88, 606/89, 90, 96, 102, 54, 60, 79, 82

(56) References Cited

U.S. PATENT DOCUMENTS 5,364,401 * 11/1994 Ferrante et al. ..................... 606/84
5,624,444 * 4/1997 Wixon et al. ....................... 606/88

* cited by examiner

Primary Examiner—David O. Reip
(74) Attorney, Agent, or Firm—Ladas & Parry

(57) ABSTRACT

An extramedullary femoral clamp guide system enables cutting a portion of the distal end of a femur perpendicularly to an ideal weight bearing axis of the femur as viewed in an antero-posterior image of the femur and cutting the frontal surface of a distal end part of the femur in parallel to the frontal surface of the distal end part of the femur. The extramedullary femoral clamp guide system comprises a first clamp (2) having a pair of holding members (6a, 6b) for clamping a first portion of a distal end part (61) of a femur therebetween, a second clamp having (3) a pair of holding members (11a, 11b) for clamping a second portion of the distal end part (61) of the femur nearer than the first portion of the same to a proximal end of the femur, a connecting mechanism (4) connecting the first and the second clamp (2, 3) so that the first clamp (2) can be translated relative to the second clamp (3), and an extramedullary rod (5) connected to the connecting mechanism (4) so as to extend outside the femur on a straight line passing a middle point between the pair of holding members (6a, 6b) of the first clamp (2) and that between the pair of holding members (11a, 11b) of the second clamp (3).

20 Claims, 9 Drawing Sheets

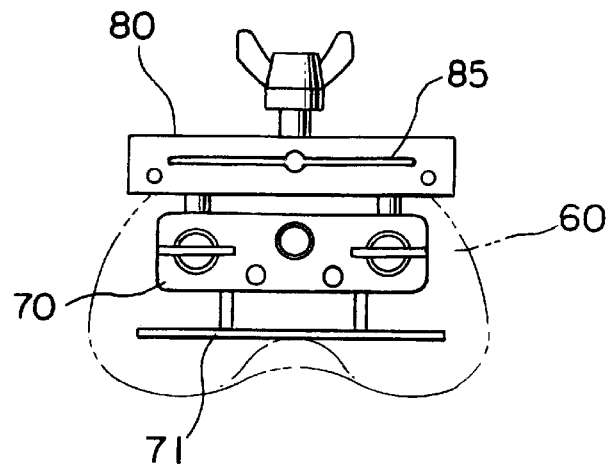
F I G. 12
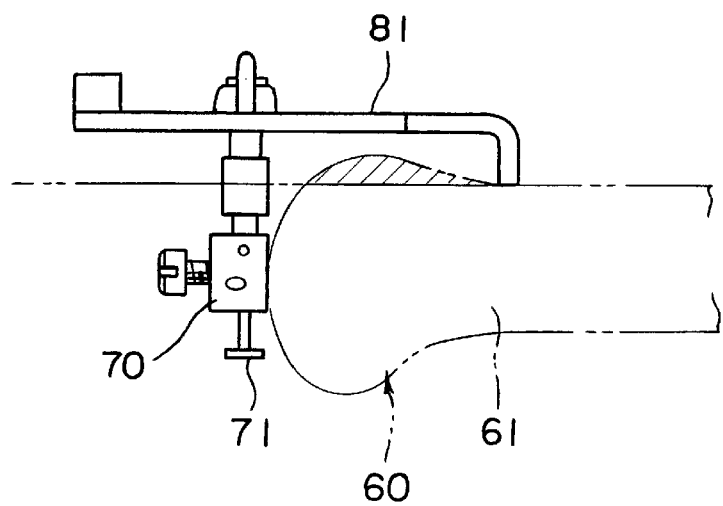
F I G. 13
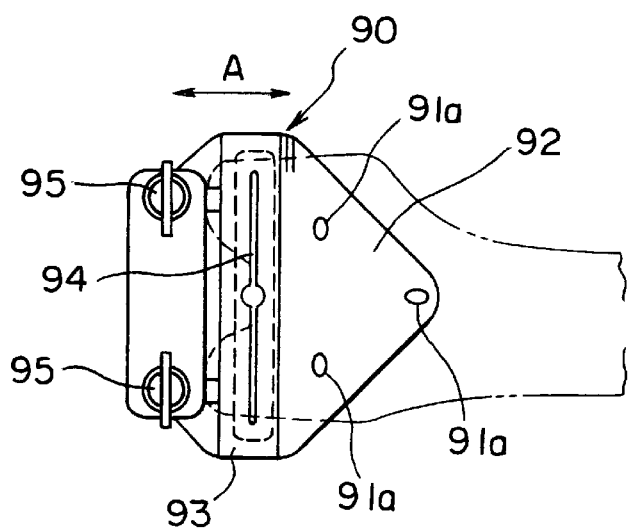
F I G. 14

EXTRAMEDULLARY FEMORAL CLAMP GUIDE SYSTEM FOR TOTAL KNEE ARTHROPLASTY

BACKGROUND OF THE INVENTION

1. Field of the Invention

The present invention relates to an extramedullary femoral clamp guide system for total knee arthroplasty that enables cutting a portion of the distal end of a femur perpendicularly to an ideal weight bearing axis of the femur as viewed in an antero-posterior image of the femur and cutting a portion of the frontal surface of a distal end part of the femur in parallel to he frontal surface of the distal end part of the femur.

2. Description of the Related Art

There are two systems for determining the angular position of a femoral component in total knee arthroplasty, i.e., an intramedullary guide system that inserts a rod into the medullary cannel of a femur, and an extramedullary guide system that connects a rod to a femur cutting guide, places the rod on the skin of the thigh and determines a cutting angle with respect to the femoral head as a landmark by using an X-ray image during operation.

The intramedullary guide system uses the anatomical morphology of the femur. It is reported in reports on clinical results of total knee arthroplasty that the intramedullary guide system is excellent in the accuracy of cutting angle.

The extramedullary guide system selects the femoral head as a landmark indirectly from an X-ray image during operation. Therefore, it is difficult to determine the center of the femoral head accurately. It is reported in reports on clinical results of the extramedullary guide system that cutting angle contains a large error.

An instrument for determining the mechanical axis of the femur with respect to the knee disclosed in JP-A No. Hei 8-33662 applies a tensile force to a distal end portion of the femur while the thigh is suspended by a suspender to determine an ideal weight bearing axis.

In the current total knee arthroplasty, the intramedullary guide system is used prevalently because the intramedullary guide system is superior in the accuracy of cutting angle to the extramedullary guide system.

Although the intramedullary guide system is excellent in the accuracy of cutting angle, the decision of a rod inserting portion and rod inserting angle is dependent mostly on the intuition of the surgeon. When an intramedullary guide inserting portion has bone spines, the rod inserting angle is prone to contain an error. Since the position of the tip of the rod is not fixed when the medullary canal is wide, cutting angle is prone to contain an error.

The intramedullary guide system cannot be applied to a curved or warped femur because it is difficult to insert the intramedullary rod into the medullary canal of a curved or warped femur.

It is reported that the bone is chipped when a guide is inserted in the distal end part of a femur for the intramedullary guide system, the normal circulation of the blood is obstructed due to the crushing and destruction of femoral medullary tissues, and serious fat embolism that cause sudden obstruction of blood vessels of the principal organs is created by the intramedullary guide system.

The invention disclosed in JP-A No. Hei 8-33662 needs a special suspender for suspending the entire leg, a device for fixedly holding the suspender on an operating table and troublesome operations, and hence the operation takes time.

Furthermore, it is possible that a clean operating field becomes unclean because the position of the leg is unstable and the clean suspender is inserted through the unclean fixing device into the clean operating field.

SUMMARY OF THE INVENTION

The present invention has been made in view of the foregoing problems and it is an object of the present invention to provide an extramedullary femoral clamp guide system for total knee arthroplasty, using the anatomical shape of the femoral distal shaft as a reference shape and capable of ensuring an accuracy equal to or higher than that can be ensured by the intramedullary femoral guide system.

According to the present invention, an extramedullary femoral clamp guide system includes a first clamp having a pair of holding members for clamping a first portion of a distal end part of a femur therebetween; a second clamp having a pair of holding members for clamping a second portion of the distal end part the femur nearer than the first portion of the same to the proximal end of the femur; a connecting mechanism connecting the first and the second clamp so that the first clamp can be translated relative to the second clamp; and an extramedullary rod connected to the connecting mechanism so as to extend outside the femur on a straight line passing the middle point between the pair of holding members of the first clamp and that of the pair of holding members of the second clamp. In total knee arthroplasty, the joint surface of the distal end of the femur can be cut along a plane perpendicular to an ideal weight bearing axis of the femur as viewed in an antero-posterior image of the femur, and the anterior surface of the distal end of the femur can be cut along a plane parallel to the anterior surface of the distal end of the femur.

BRIEF DESCRIPTION OF THE DRAWINGS

FIG. 12 is an end view of a femoral distal frontal surface cutting guide mounted on a cutting block;

FIG. 13 is a side elevation of the femoral distal frontal surface cutting guide shown in FIG. 12 with a stylus attached thereto;

FIG. 14 is a plan view of a movable femoral distal frontal surface cutting guide mounted on a cutting block;

DESCRIPTION OF THE PREFERRED EMBODIMENTS

Preferred embodiments of the present invention will be described with reference to the accompanying drawings.

Figure 1:
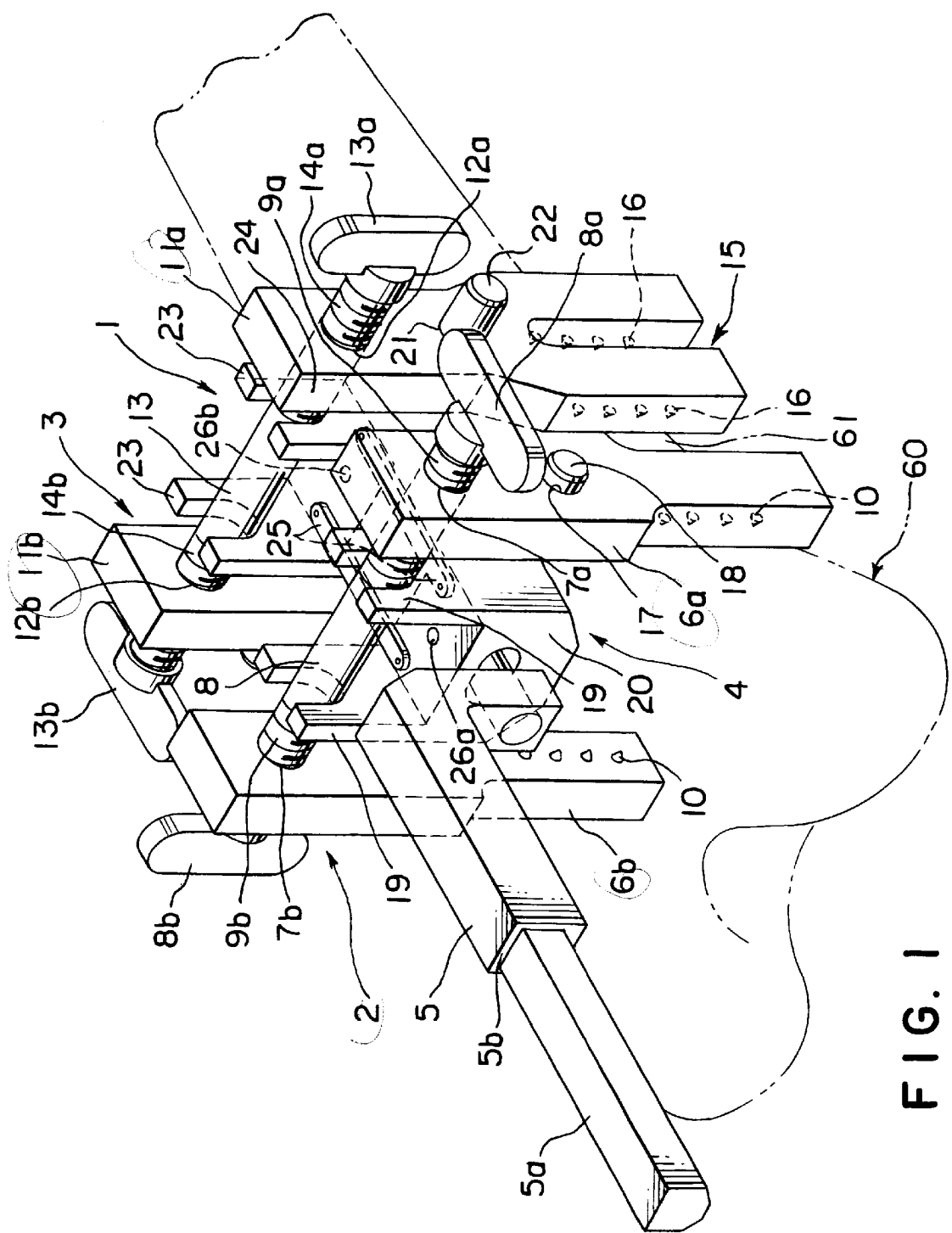
FIG. 1 is a perspective view of an extramedullary femoral clamp guide system in a first embodiment according to the present invention for total knee arthroplasty.

Referring to FIG. 1, an extramedullary femoral clamp guide system 1 for total knee arthroplasty includes a first clamp 2 that holds to a first portion of a distal end part 61 of a femur 60, a second clamp 3 that holds to a second portion of the distal end part 61 of the femur 60 nearer than the first portion of the same to the proximal end of the femur 60, a connecting mechanism 4 connecting the first clamp 2 and the second clamp 3 so that the first clamp 2 can be translated relative to the second clamp 3, and an extramedullary rod 5 having one end connected to the connecting mechanism 4 and the other end projecting from the distal end of the femur 60.

The first clamp 2 has a pair of holding members 6a and 6b provided with a left-hand threaded hole 7a and a right-hand threaded hole 7b in their upper portions, respectively, and a first screw rod 8 having one left-hand threaded end portion 9a and the other right-hand threaded end portion 9b screwed in the threaded holes 7a and 7b, respectively, to move the holding members 6a and 6b toward and away from each other. Flat lugs 8a and 8b are formed integrally with the first screw rod 8 to facilitate turning the first screw rod 8. The holding members 6a and 6b are provided on their inner surfaces with spikes 10 for securely holding the holding members 6a and 6b on the distal end part 61 of the femur 60.

The second clamp 3 has a pair of holding members 11a and 11b provided with a left-hand threaded hole 12a and a right-hand threaded hole 12b in their upper portions, respectively, and a second screw rod 13 having one left-hand threaded end portion 14a and the other right-hand threaded end portion 14b screwed in the threaded holes 12a and 12b, respectively, to move the holding members 11a and 11b toward and away from each other. Flat lugs 13a and 13b are formed integrally with the second screw rod 13 to facilitate turning the second screw rod 13. The holding member 11a has a bifurcate holding part 15 The holding members 11a and 11b are provided on their inner surfaces with spikes 16 similar to the spikes 10 formed on the inner surfaces of the holding members 6a and 6b.

The second clamp 3 clamps the distal end part 61 at three points. The second lamp 3 are fixed vertically to the distal end part 61 with the bifurcate portion 15 of the holding member 11a set horizontally in close contact with the distal end part 61. Thus, the second clamp 3 is never set obliquely.

The connecting mechanism 4 includes a first main block 20 provided with first connecting rods 18 inserted in holes 17 formed in middle portions of the holding members 6a and 6b of the first clamp 2 and having first support portions 19 supporting the first screw rod 8, a second main block 24 provided with second connecting rods 22 inserted in holes 21 formed in middle portions of the holding members 11a and 11b of the second clamp 3 and having second support portions 23 supporting the second screw rod 13, and a pair of links 25 connecting the first main block 20 and the second main block 24 so that the first main block 20 and the second main block 24 are able to be translated relative to each other.

The extramedullary rod 5 has one end portion supported for turning by a pin 26a on a portion of the first main block 20 corresponding to a middle point between the pair of holding members 6a and 6b of the first clamp 2 and by a pin 26b on a portion of the second main block 24 corresponding to a middle point between the pair of holding members 11a and 11b of the second clamp 3. A forward end portion 5a of the extramedullary rod 5 has a reduced section, and a shoulder 5b is formed between the forward end portion 5a of the extramedullary rod 5 and a base end portion of the same.

The extramedullary rod 5 is disposed so that its axis extends outside the femur 60 on a straight line passing the middle point between the pair of holding members 6a and 6b of the first clamp 2 and the middle point between the pair of holding members 11a and 11b of the second clamp 3.

Figure 2:
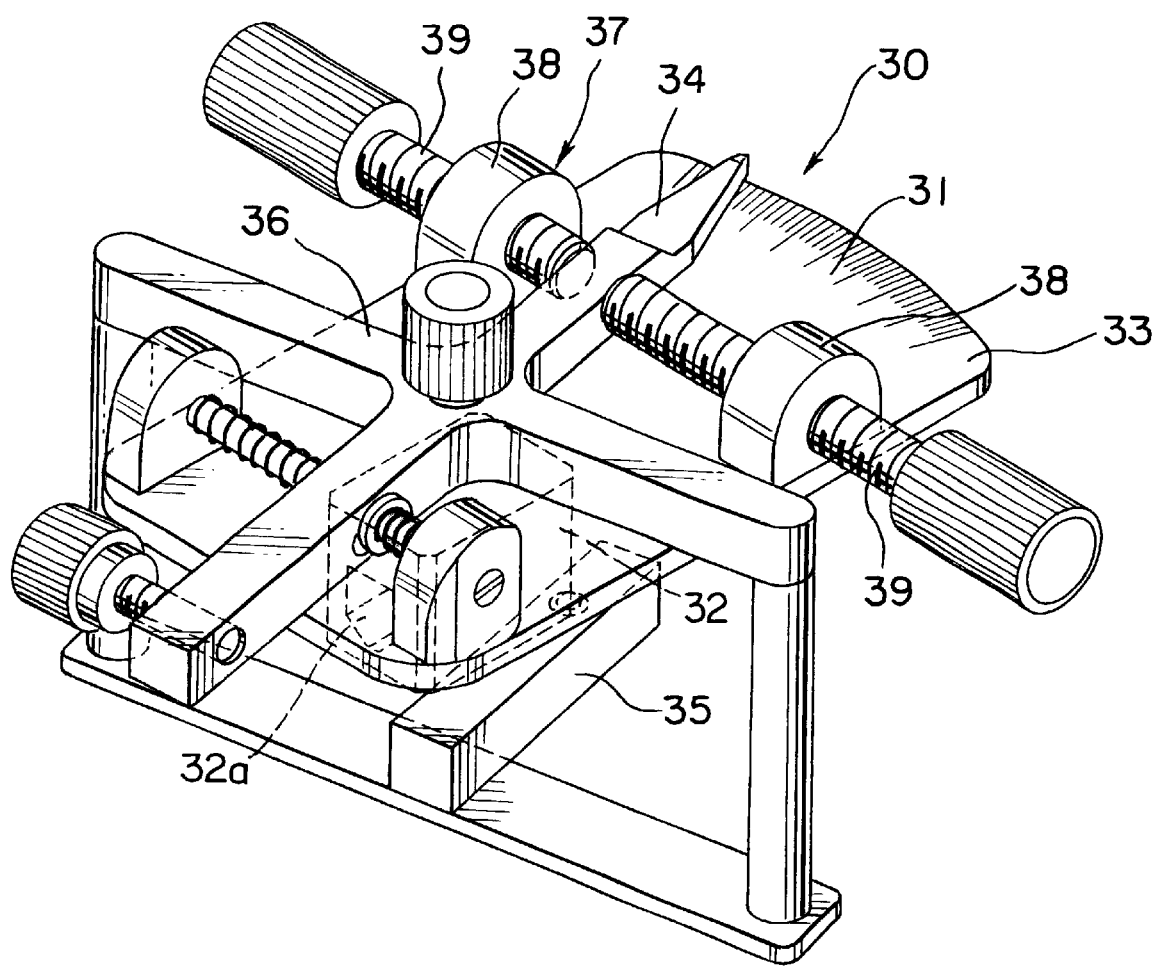
FIG. 2 is a perspective view of a valgus angle adjusting device included in the extramedullary femoral clamp guide system shown in FIG. 1.
Figure 10:
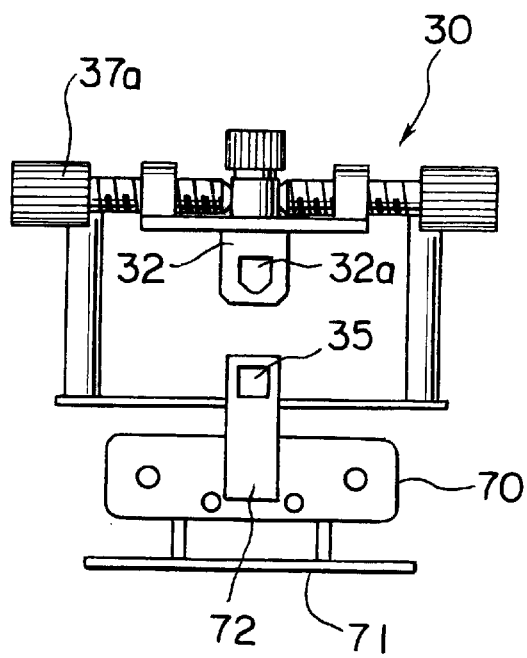
FIG. 10 is an end view of the valgus angle adjusting device shown in FIG. 2.

A valgus angle adjusting device 30 shown in FIG. 2 is detachably mounted on the extramedullary femoral clamp guide system 1. The valgus angle adjusting device 30 includes a valgus angle indicating plate 33 having a surface provided with an angle scale 31 and a back surface provided with a bracket 32 (FIG. 10) provided with a through hole 32a for receiving the forward end portion 5a of the extramedullary rod 5 therein, an indexing unit 36 having an indicator 34 and connected to the valgus angle indicating plate 33 so as to be turnable relative to the valgus angle indicating plate 33, and a fixing mechanism 37 for fixing the indicator 34 of the indexing unit 36 relative to the valgus angle indicating plate 33. A cutting block holding member 35 is supported on the indexing unit 36 so as to be turnable together with the indicator 34 in a horizontal plane relative to the valgus angle indicating plate 33. The fixing mechanism 37 includes a pair of brackets 38 provided with threaded holes, respectively, and disposed opposite to each other on the surface of the valgus angle indicating plate 33, and fixing screw rods 39 having threaded portions screwed in the threaded holes of the brackets 38, respectively.

Figure 3:
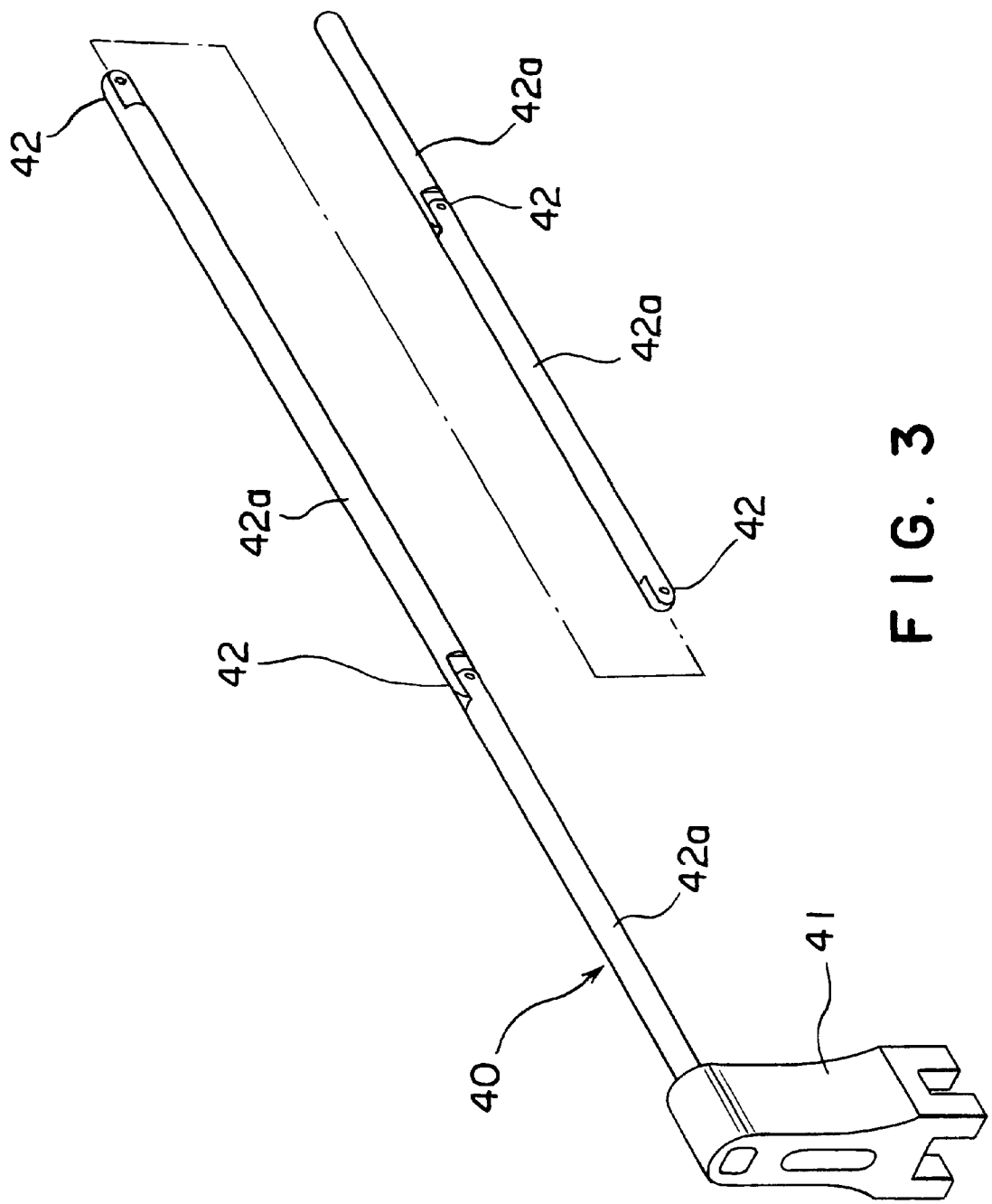
FIG. 3 is a perspective view of an alignment confirmation device included in the valgus angle adjusting device shown in FIG. 2.

Referring to FIG. 3, an alignment confirmation device 40 to be detachably mounted on the valgus angle adjusting device 30 includes a connecting member 41 to be put on a base end part of the indicator 34, and a bendable rod formed by successively joining a plurality of rods 42a by joints 42 for turning relative to each other in a vertical plane. The passage of the bendable rod of the alignment confirmation device 40 through the center of the femoral head and the perpendicularity of a valgus cutting line to the weight bearing axis can be estimated by palpation by setting a distal end part of the link-type alignment confirmation device 40 in close contact with the skin. The passage of the bendable rod of the alignment confirmation device 40 through the center of the femoral head and the perpendicularity of the valgus cutting line to the weight bearing axis can be confirmed from an X-ray image. When it is found that the valgus cutting line deviates greatly from the weight bearing axis by palpation using the alignment confirmation device 40, it is necessary to confirm whether a graphic cutting angle is correct and whether the extramedullary femoral clamp system 1 is attached correctly to the femur.

According to the present invention, the position of the femoral head can be accurately estimated by pressing the distal end part of the link-type alignment confirmation device 40 against the skin to reduce the distance between the distal end of the alignment confirmation device 40 and the femoral head to the least possible extent. An alignment rod employed in a conventional extramedullary femoral clamp guide system is a simple straight rod that cannot be bent. Consequently, the distal end of the alignment rod cannot be pressed against the skin and a gap is formed between the distal end of the alignment rod and the skin. Thus, it is difficult to estimate the position of the femoral head by using the alignment rod and an estimated position of the femoral head includes an error.

Figure 4:
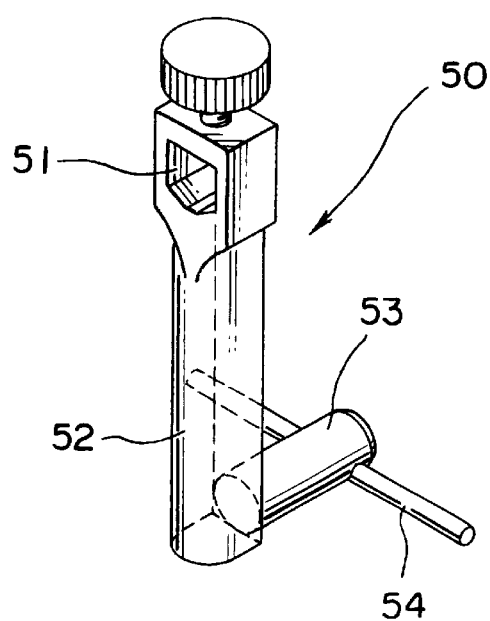
FIG. 4 is a perspective view of a locating stopper included in the extramedullary femoral clamp guide system shown in FIG. 1.

Referring to FIG. 4, a locating stopper 50 capable of being detachably mounted on the extramedullary clamp guide system 1 includes a main body 52 provided with an opening for receiving the extramedullary rod 5, a rod 53 projecting from the main body 52 with its axis in parallel to that of the extramedullary rod 5 as inserted in the opening 51 of the main body 52, and a angular position confirmation bar 54 attached to the rod 53. The locating stopper 50 is mounted on the extramedullary rod 5 and is fixed in place with the main body 52 in contact with the shoulder 5b of the extramedullary rod 5. The angular position confirmation rod 54 is used to prevent the extramedullary clamp guide system 1 from being mounted on the distal end part 61 of the femur 60 in a tilted position.

The extremity of the rod 53 of the locating stopper 50 is set in contact with the intercondyle notch in the joint surface of the distal end of the femur 60 so that the second clamp 3 of the extramedullary clamp guide system 1 is spaced 9 cm apart from the distal end of the femur 60.

Figure 5:
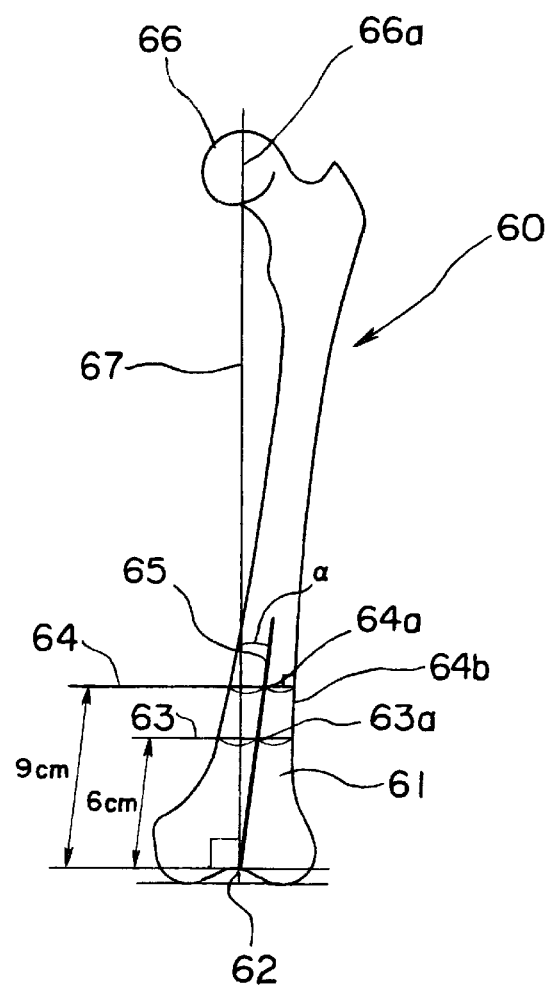
FIG. 5 is an antero-posterior X-ray image of a femur, showing dimensions measured before an operation.

FIG. 5 is an X-ray image of the femur 60 showing a preoperative measurement diagram of the femur 60. The preoperative measurement diagram of the femur 60 is produced by the following method.

In an antero-posterior X-ray image, a line 64 is drawn so as to intersect the outer side edge 64b of the cortex of the femur 60 perpendicularly at a position on the side edge 64b at a distance of 9 cm from the intercondyle notch 62 on the joint surface of the distal end of the distal end part 61 of the femur 60. A line 63 is drawn in parallel to the line 64 so as to intersect the distal end part 61 at a position at 6 cm from the intercondyle notch 62 on the joint surface of the distal end of the distal end part 61. A straight line passing the middle point 63a on a section of the line 63 included in the distal end part 61 and the middle point 64a on a section of the line 64 included in the distal end part 61 is drawn. This straight line is use as a femoral distal reference line 65.

Subsequently, the center 66a of the femoral head 66 and the intercondyle notch 62 on the joint surface of the distal end of the distal end part 61 of the femur 60 are connected by a straight line, which is regarded as an ideal weight bearing axis 67. The angle between the ideal weight bearing axis 67 and the femoral distal reference line 65 is the valgus cutting angle α of the distal end of the femur 60. The valgus cutting angle α can be easily measured by a special template or a protractor. The valgus angle adjusting device 30 is set for the valgus cutting angle α.

A method of using the extramedullary femoral clamp guide system 1 will be described hereinafter.

Figure 6:
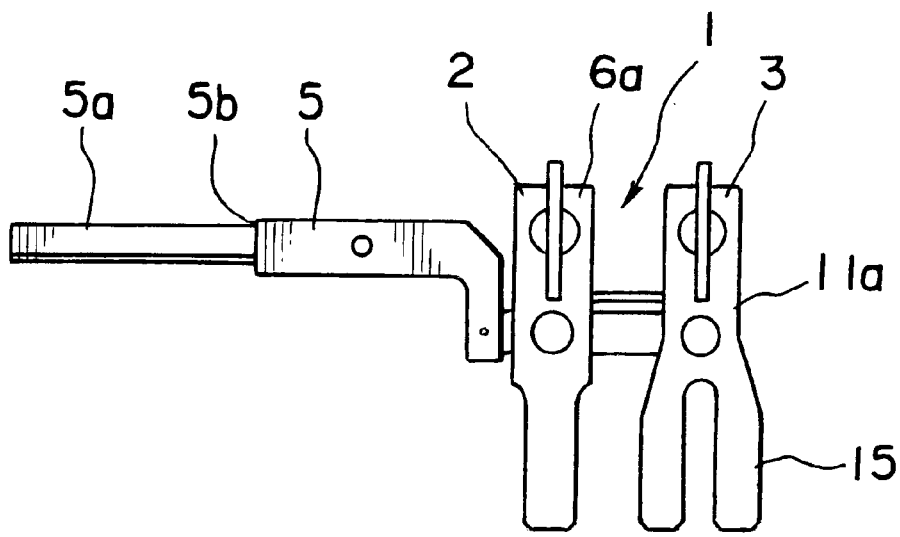
FIG. 6 is a side elevation of the extramedullary femoral clamp guide system shown in FIG. 1 in a state before the locating stopper is put thereon.
Figure 7:
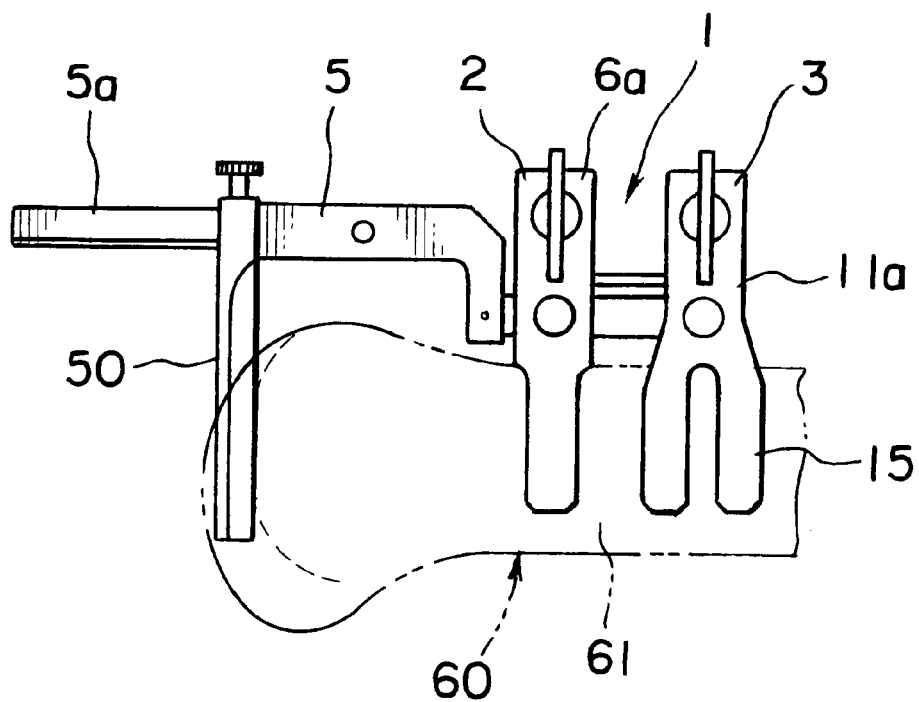
FIG. 7 is a side elevation of the extramedullary femoral clamp guide system shown in FIG. 1 as disposed on a distal end part of the femoral shaft with the locating stopper put thereon.

The locating stopper 50 shown in FIG. 7 is mounted on the forward end portion 5a of the extramedullary rod 5 of the extramedullary femoral clamp guide system 1 shown in FIG. 6. The locating stopper 50 is moved along the forward end portion 5a to bring the locating stopper 50 into contact with the shoulder 5b of the extramedullary rod 5 and the locating stopper 50 is fixed to the extramedullary rod 5.

Then, as shown in FIG. 7, the extramedullary femoral clamp guide system 1 fixedly provided with the locating stopper 50 is put on the distal end part 61 of the femur 60 and is moved toward the proximal end of the femur 60 to bring the extremity of the rod 53 of the locating stopper 50 into contact with the intercondyle notch 62 on the joint surface of the distal end of the distal end part 61 of the femur 60. The extramedullary femoral clamp guide system 1 is set after setting the angular position adjusting bar 54 attached to the rod 53 in parallel to the femoral condyle surface to avoid setting the extramedullary femoral clamp guide system 1 on the distal end part 61 with the extramedullary femoral clamp guide system 1 tilted to the longitudinal axis of the femur 60. Thus, the first clamp 2 and the second clamp 3 of the extramedullary femoral clamp guide system 1 are disposed on the distal end part 61 of the femur 60 at positions determined by construction. In this state, the lower surfaces of the first main block 20 and the second main block 24 are in close contact with the frontal surface of the distal end part 61 of the femur 60 to set the first clamp 2 and the second clamp 3 in parallel to the frontal surface of the distal end part 61 of the femur 60 as viewed in a side elevation.

The flat lugs 13a and 13b of the screw rod 13 screwed in the pair of holding members 11a and 11b of the second clamp 3 of the extramedullary femoral clamp guide system 1 are turned in one direction to move the holding members 11a and 11b toward each other along the connecting rods 22 of the connecting mechanism 4 to stick the spikes 16 formed on the inner surfaces of the holding members 11a and 11b into the surface of the distal end part 61, so that the second clamp 3 is secured at the predetermined position on the distal end part 61, i.e., the position at 9 cm from the intercondyle notch 62 of the distal end of the distal end part 61. Since the holding member 11a of the second clamp 3 has the bifurcate part 15, the second clamp 3 is fixed to the distal end part 61 in parallel to the distal end part 61 so as to extend perpendicularly to the distal end part 61.

After thus securing the second clamp 3 to the distal end portion 61, the locating stopper 50 is removed from the extramedullary rod 5, the flat lugs 8a and 8b of the screw rod 8 screwed in the threaded holes of the pair of holding members 61 and 6b of the first clamp 2 are turned in one direction to move the pair of holding members 6a and 6b toward each other along the connecting rods 18 of the connecting mechanism 4. Thus, the spikes 10 formed on the inner surfaces of the holding members 6a and 6b into the surface of the distal end part 61 to secure the first clam 2 to the distal end part 61 at the position at 6 cm from the intercondyle notch 62 on the joint surface of the distal end of the distal end part 61.

In a state where the extramedullary femoral clamp guide system 1 is set on the distal end part 61 with the first clamp 2 and the second clamp 3 secured to the distal end part 61, the center axis of the extramedullary rod 5 is aligned with a straight line passing the respective middle points of the first clamp 2 and the second clamp 3. Therefore, the center axis of the extramedullary rod 5 is aligned with the femoral distal reference line 65 drawn by construction using the preoperative measurement diagram of the femur 60 shown in FIG. 5.

Figure 8:
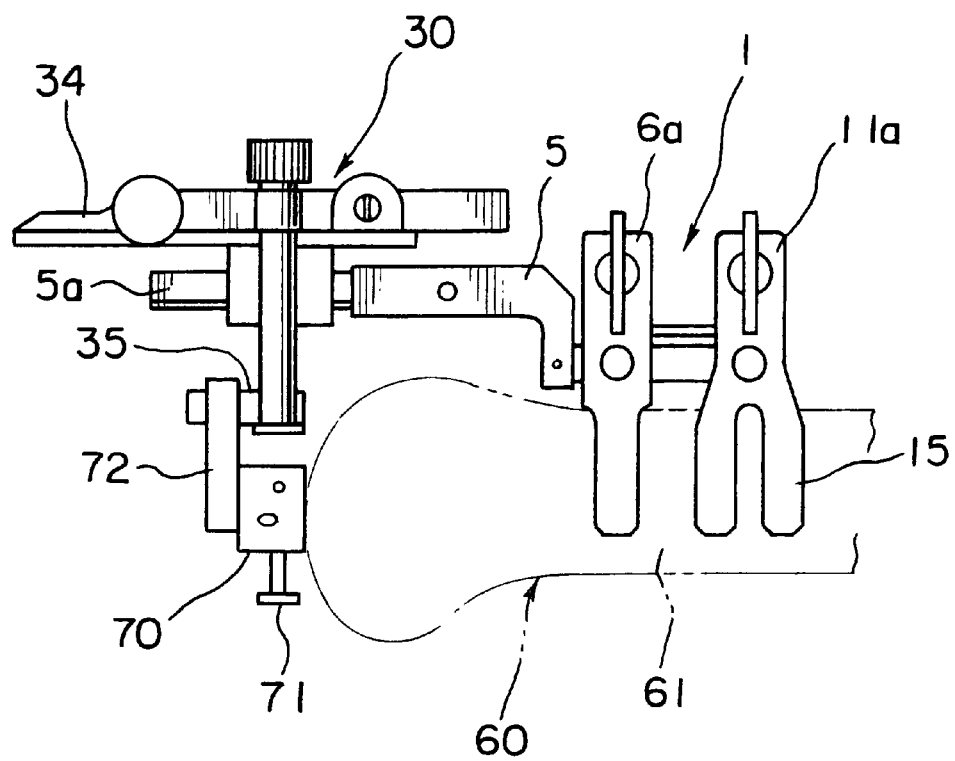
FIG. 8 is a side elevation of the extramedullary femoral clamp guide in a state shown in FIG. 7 with the valgus angle adjusting device put thereon.
Figure 9:
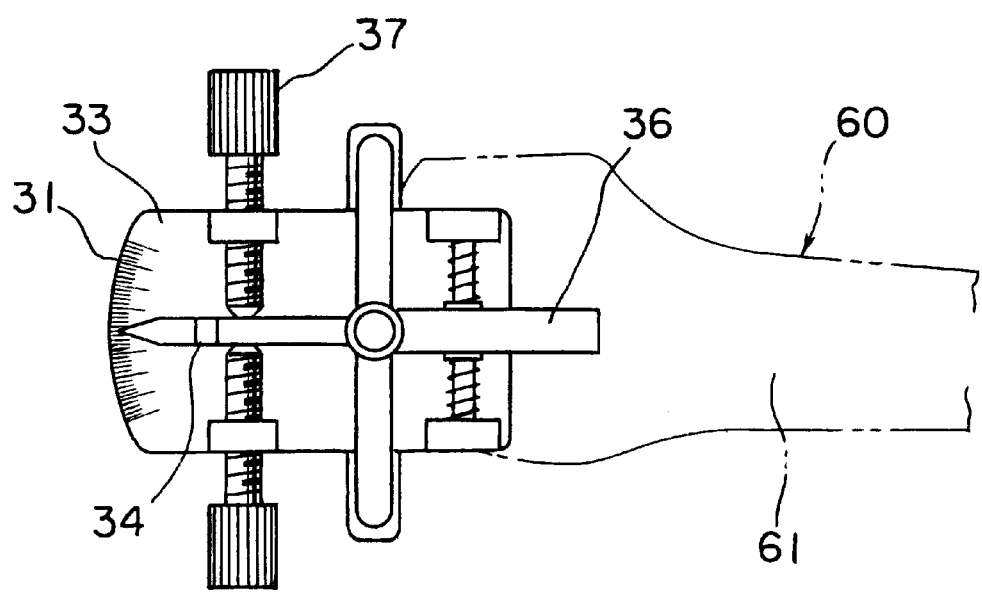
FIG. 9 is a front elevation of the valgus angle adjusting device shown in FIG. 2.

Subsequently, the valgus angle adjusting device 30 set for the valgus cutting angle α is mounted on the extramedullary rod 5 as shown in FIG. 8. In this state, the center axis of the cutting block holding member 35 is aligned with the ideal weight bearing axis 67 determined by construction using the preoperative measurement diagram shown in FIG. 5 and the valgus cutting line is perpendicular to the ideal weigh bearing axis 67.

Figure 11:
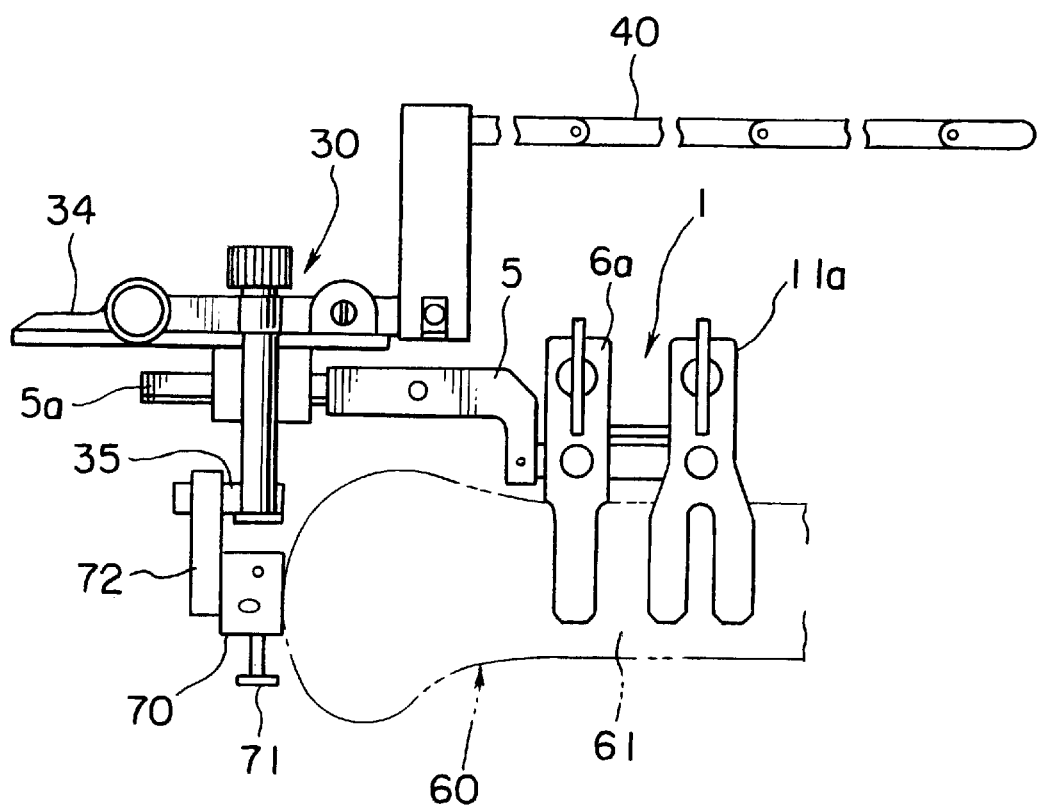
FIG. 11 is a side elevation similar to FIG. 8, in which the alignment confirmation device is attached to the valgus angle adjusting device.

The alignment of the center axis of the cutting block holding member 35 of the valgus angle adjusting device 30 with the ideal weight bearing axis 67 is confirmed by using the alignment confirmation device 40 shown in FIG. 3 mounted on the valgus angle adjusting device 30. As shown in FIG. 11, the alignment confirmation device 40 is put on the base end part of the indicator 34 for indicating a valgus angle and the passage of the bendable rod of the alignment confirmation device 40 through the center of the femoral head is confirmed by palpation.

Subsequently, a cutting block 70 shown in FIG. 8 is connected to the cutting block holding member 35 by a connecting device 72. The position of the cutting block 70 is adjusted by an angle adjusting plate 71 so that the cutting block 70 is parallel to is inclined at an angle (which is dependent on the type of an artificial knee joint to be used and is 3° in this case) to a femoral condyle surface. The cutting block 70 thus located is fixed to the distal end of the femur 60 with four steel pins.

After thus fixing the cutting block 70 to the distal end of the femur 60, all the components of the extramedullary femoral clamp guide system 1 excluding the cutting block 70 are removed from the distal end part 61 of the femur 60. Subsequently, a frontal surface cutting guide 80 shown in FIG. 12 is mounted on the cutting block 70, and a cutting level is determined by using a stylus 81 shown in FIG. 13. The cutting guide 80 is provided with a guide slit 85, which is parallel to the respective lower surfaces of the first main block 20 and the second main block 24. A frontal part of the distal end part 61 can be cut along a plane parallel to the frontal surface of the distal end part 61 by using the cutting guide 80 provided with the guide slit 85.

Figure 15:
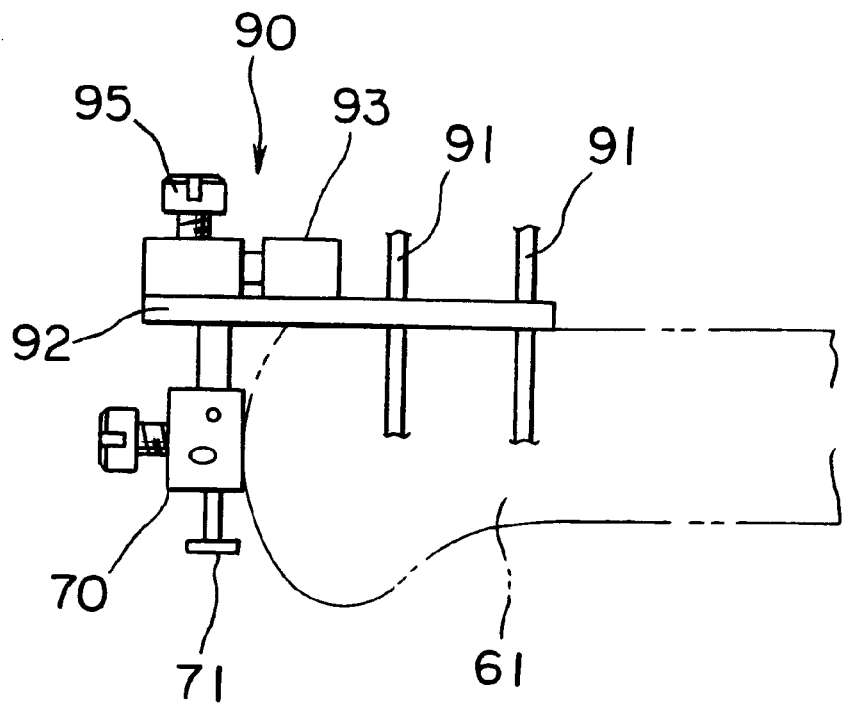
FIG. 15 is a side elevation of the movable femoral distal frontal surface cutting guide mounted on a cutting block.

Subsequently, a femoral distal end cutting guide 90 shown in FIGS. 14 and 15 is mounted on the cutting block 70. The femoral distal end cutting guide 90 has a base plate 92 provided with three holes 91a, and a guide member 93 placed on the base plate 92 so as to be movable in the directions of the arrows A. The base plate 9w is fixed to the distal end part 61 by sticking three steel pins 91 through the holes 91a into the distal end part 61 of the femur 60. The guide member 93 is provided with a guide slit 94 perpendicular to the directions in which the guide member 93 is moved.

The position of the guide lit 94 of the guide member 93 of the femoral distal end cutting guide 90 relative to the femur 60 is adjusted by moving the guide member 93 in the directions of the arrows A. The guide member 93 is fastened to the base plate 92 with fastening screws 95 after the guide member 93 has been located at an proper position for cutting a portion of a proper thickness of the distal end of the distal end part 61.

After thus fixing the femoral distal end cutting guide 90 to the distal end part 61, a portion of the distal end of the distal end part 61 is cut to complete a femoral cutting operation using the extramedullary femoral clamp guide system 1.

The distal end of the distal end part 61 is finished by cutting the same by using a special final femoral distal end cutting guide for cutting the femoral distal end to prepare the distal end for using a special artificial knee joint.

Figure 16:
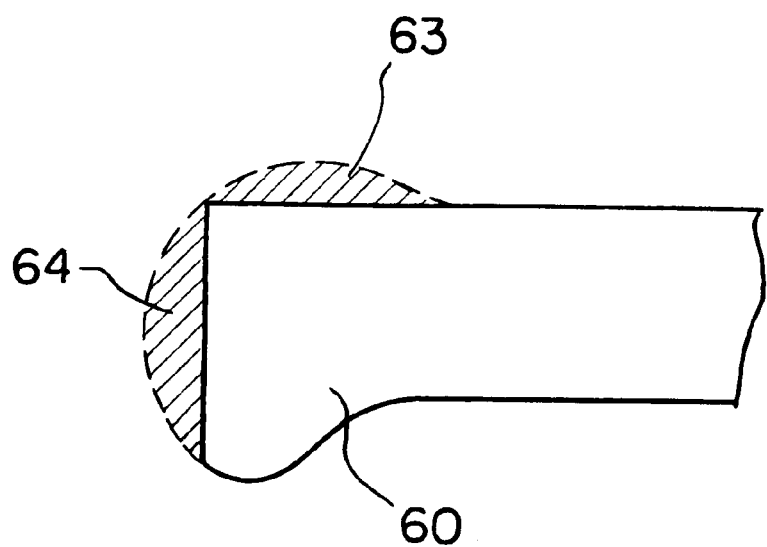
FIG. 16 is a side elevation of a femur having a cut distal frontal surface and a cut distal end surface.

FIG. 16 shows the distal end part 61 of the femur 60 thus cut by using the extramedullary femoral clamp guide system 1, in which shaded portions are a cut frontal portion 63 and a cut distal end portion 64.

When carrying out total knee arthroplasty, the angular position of a femoral component can be determined on the basis of the anatomical morphology of a distal end part of a femur by using the extramedullary femoral clamp guide system of the present invention, a portion of the distal end of the femur can be cut along a plane perpendicular to the ideal weight bearing axis of the femur as viewed in an antero-posterior image of the femur, a frontal portion of the distal end part of the femur can be cut along a plane parallel to the frontal surface of the distal end part of the femur as viewed in a side elevation of the femur.

Since the extramedullary femoral clamp guide system of the present invention uses the anatomical morphology of the distal end part of the femur as a reference shape, any operator can accurately determine a cutting angle without requiring any special skill, and the accuracy of the cutting angle determined by using the extramedullary femoral clamp guide system is equal to or higher than that of a cutting angle determined by using the prevalently used intramedullary guide system.

Moreover, since the cutting block mounted on the extramedullary femoral clamp guide system of the present invention has a valgus angle adjusting function, a frontal portion and an end portion of a distal end part of a warped femur can be satisfactorily cut.

The extramedullary femoral clamp guide system of the present invention can be used for cutting a distal end part of a femur for preparation to use any one of different artificial knee joints because the distal end part cut by using the extramedullary femoral clap guide system is finished by using a special final cutting guide for using the selected artificial kneed joint.

As apparent from the foregoing description, according to the present invention, the rod can be accurately set at a correct position in a correct angle without depending on the operator's intuition because the extramedullary femoral clamp guide system uses the anatomical morphology of the distal end part of the femur as a reference shape. Therefore, the accuracy of the cutting angle determined by using the extramedullary femoral clamp guide system is equal to or higher than that of a cutting angle determined by using the prevalently used intramedullary guide system.

Furthermore, since the cutting block mounted on the extramedullary femoral clamp guide system of the present invention has a valgus angle adjusting function, the cutting block can be set in an angular position conforming to a valgus angle. Thus, the cutting block can be correctly set for accurate cutting by using a single cutting guide, whereas a femur cutting operation using the conventional guide system needs different cutting guides respectively for setting a cutting block at different angular positions.

What is claimed is:

1. An extramedullary femoral clamp guide system for total knee arthroplasty comprising:

a first clamp (2) having a pair of holding members (6a, 6b) for clamping a first portion of a distal end part of a femur therebetween;

a second clamp having (3) a pair of holding members (11a, 11b) for clamping a second portion of the distal end part of the femur nearer than the first portion of the same to a proximal end of the femur;

a connecting mechanism (4) connecting the first and the second clamp (2, 3) so that the first clamp (2) can be moved parallel to the second clamp (3); and an extramedullary rod (5) connected to the connecting mechanism (4) so as to extend outside the femur on a straight line passing a middle point between the pair of holding members (6a, 6b) of the first clamp (2) and that between the pair of holding members (11a, 11b) of the second clamp (3).

2. The extramedullary femoral clamp guide system according to claim 1, wherein a locating stopper (50) is mounted on the extramedullary rod (5).

3. The extramedullary femoral clamp guide system according to claim 2, wherein one (11a) of the holding members (11a, 11b) of the second clamp (3) has a bifurcate part (15).

4. The extramedullary femoral clamp guide system according to claim 3, wherein the holding members (61, 6b, 11a, 11b) are provided on their inner surfaces with spikes (10, 16), respectively.

5. The extramedullary femoral clamp guide system according to claim 4, wherein a valgus angle adjusting device (30) is detachably mounted on the extramedullary rod (5).

6. The extramedullary femoral clamp guide system according to claim 3, wherein a valgus angle adjusting device (30) is detachably mounted on the extramedullary rod (5).

7. The extramedullary femoral clamp guide system according to claim 2, wherein the holding members (61, 6b, 11a, 11b) are provided on their inner surfaces with spikes (10, 16), respectively.

8. The extramedullary femoral clamp guide system according to claim 7, wherein a valgus angle adjusting device (30) is detachably mounted on the extramedullary rod (5).

9. The extramedullary femoral clamp guide system according to claim 1, wherein one (11a) of the holding members (11a, 11b) of the second clamp (3) has a bifurcate part (15).

10. The extramedullary femoral clamp guide system according to claim 9, wherein the holding members (61, 6b, 11a, 11b) are provided on their inner surfaces with spikes (10, 16), respectively.

11. The extramedullary femoral clamp guide system according to claim 10, wherein a valgus angle adjusting device (30) is detachably mounted on the extramedullary rod (5).

12. The extramedullary femoral clamp guide system according to claim 9, wherein a valgus angle adjusting device (30) is detachably mounted on the extramedullary rod (5).

13. The extramedullary femoral clamp guide system according to claim 1, wherein the holding members (61, 6b, 11a, 11b) are provided on their inner surfaces with spikes (10, 16), respectively.

14. The extramedullary femoral clamp guide system according to claim 13, wherein a valgus angle adjusting device (30) is detachably mounted on the extramedullary rod (5).

15. The extramedullary femoral clamp guide system according to claim 1, wherein a valgus angle adjusting device (30) is detachably mounted on the extramedullary rod (5).

16. The extramedullary femoral clamp guide system according to claim 15, wherein the valgus angle adjusting device (30) includes a valgus angle indicating plate (33) having a surface provided with an angle scale (31) and a back surface provided with a bracket (32) provided with a through hole (32a) for receiving the extramedullary rod (5) therein, an indexing unit (36) having an indicator (34) and a cutting block holding member (35), and connected to the valgus angle indicating plate (33) so as to be turnable relative to the valgus angle indicating plate (33), and a fixing means (37) for fixing the indicator (34) of the indexing unit (36) relative to the valgus angle indicating plate (33).

17. The extramedullary femoral clamp guide system according to claim 15, wherein a cutting block (70) is fixedly held at the distal end of the distal end part of the femur by the valgus angle adjusting device (3) mounted on the extramedullary rod (5), a frontal surface cutting guide (80) is mounted on the cutting block (70) to cut a frontal portion of the distal end part of the femur along a plane parallel to a frontal surface of the distal end part of the femur.

18. The extramedullary femoral clamp guide system according to claim 15, wherein an alignment confirmation device (40) is attached to the valgus angle adjusting device (30) to confirm the passage of the weight bearing axis through a center of a femoral head of the femur.

19. The extramedullary femoral clamp guide system according to 18, wherein the alignment confirmation device (40) has a bendable rod bendable in a single plane formed by successively joining a plurality of rods (42).

20. The extramedullary femoral clamp guide system according to claim 2, wherein a valgus angle adjusting device (30) is detachably mounted on the extramedullary rod (5).

* * * * *